United States Patent [19]

Dunstan et al.

[11] Patent Number: 4,972,137
[45] Date of Patent: Nov. 20, 1990

[54] ISOLATION CIRCUIT FOR BLOOD CELL COUNTER

[75] Inventors: Gerald J. Dunstan, Wheathampstead; Ian D. Gilbert, St. Albans, both of England

[73] Assignee: Coulter Electronics, Inc., Hialeah, Fla.

[21] Appl. No.: 360,874

[22] Filed: May 31, 1989

[51] Int. Cl.⁵ .................................................. G01N 27/04
[52] U.S. Cl. .................................... 324/71.4; 324/71.1
[58] Field of Search ................ 324/71.4, 71.1, 439, 324/444; 377/11, 12

[56] References Cited

U.S. PATENT DOCUMENTS

| | | | |
|---|---|---|---|
| 3,271,672 | 9/1966 | Henderson | 324/71.1 |
| 3,340,470 | 9/1967 | Coulter, Jr. | 324/71.1 |
| 3,340,471 | 9/1967 | Coulter, Jr. | 324/71.1 |
| 3,441,848 | 4/1969 | Valley et al. | 324/71.1 |
| 3,689,833 | 9/1972 | Hogg | 324/71.1 |
| 3,706,980 | 12/1972 | Maltby | 324/61 R X |
| 3,944,917 | 3/1976 | Hogg, et al. | 324/71.1 |
| 3,979,669 | 9/1976 | Godin | 324/71.1 |
| 3,982,182 | 9/1976 | Hogg | 324/71.1 |
| 4,025,307 | 5/1977 | Randolph et al. | 324/71.4 X |
| 4,180,091 | 12/1979 | Hanley et al. | 324/71.4 X |
| 4,600,880 | 7/1986 | Doutre et al. | 324/71.1 |
| 4,651,087 | 3/1987 | Shirato et al. | 324/71.4 |

Primary Examiner—Reinhard J. Eisenzopf
Assistant Examiner—Jack B. Harvey
Attorney, Agent, or Firm—Harry W. Barron; Gerald R. Hibnick

[57] ABSTRACT

A particle counter, of the type utilizing a Coulter(R) type aperature and a suction flow path downstream from the aperture, has a pair of electrodes on both sides of the aperture. A current is provided from the downstream electrode to the upstream electrode and pulses in the resulting voltage across the aperture are monitored to detect the passage of blood cells through the aperture. A grounded electrode is placed in the downstream flow path at a position near the package panel to isolate the cell counter from external electrical noise signals. An isolated high input inpedance amplifier is coupled to provide the monitored voltage to an inserted electrode positioned between the downstream aperture electrode and the grounded panel electrode. Because the inserted electrode and downstream electrode are then at the same voltage, no current flows through that portion of the flow path.

4 Claims, 2 Drawing Sheets

ISOLATION CIRCUIT FOR BLOOD CELL COUNTER

This invention relates to an improved blood cell counter, and more particularly, to such a counter having a Coulter(®) type aperture and circuitry coupled with the liquid flow paths from the aperture to eliminate electrical leakage currents through the liquid flow path.

BACKGROUND OF THE INVENTION

Blood cell counters of the Coulter type have been known for many years and were first described in the U.S. Pat. No. 2,656,508, granted Oct. 20, 1953 in the name of Wallace H. Coulter. In the basic Coulter structure, as taught by the Coulter '508 patent, a constant current is provided through a small opening, or aperture, while an electrolyte liquid solution, containing a suspension of blood cells, flows through the aperture. Each time a blood cell flows through the aperture, the internal resistance of the electrolyte within the aperture increases, thereby causing the voltage across the aperture to increase. By monitoring the voltage across the aperture, the pulse signals, which appear each time a blood cell flows through the aperture, can be detected and counted to manifest a blood cell count and volume for a fixed volume of flowing liquid.

In order to obtain the optimum operation of a Coulter type blood cell counter, it is desirable that all of the available current be applied through the aperture. This is generally accomplished by placing electrodes in the electrolyte solution at a position opposite to both sides of the aperture and providing a current from one to the other of the electrodes. The blood cell suspension or containing fluid is caused to flow through the aperture, typically, by applying a suction, or vacuum, to the downstream side of the aperture to draw the fluid through the aperture.

However, since the fluid drawn away from the aperture is an electrolyte which conducts current when a voltage difference exists from one part to another part of the flow path. Whatever current is conducted through the electrolyte, is diverted away from the aperture, thereby reducing the effectiveness of the measurements obtained from monitoring the voltage across the aperture. The voltage difference in the downstream flowpath occurs when the design of the blood cell counter causes the electrode downstream from the aperture to be at a non-reference potential and where the flow path is grounded at the point it exits the cell counter package. The reason for grounding the flow path at the point it exits the package is to prevent environmental signals, such as sixty cycle hum, due to the lights, or other environmental electrical noise, from being conducted through the electrolyte solution and causing interference in the circuitry monitoring the voltage drop across the aperture.

DESCRIPTION OF THE PRIOR ART

In the past, different techniques have been utilized to prevent the current provided for application through the aperture from being diverted through the electrolyte of the suction flow path. One technique has been to ground the downstream electrode and provide the current to the upstream electrode, which is then at a non-grounded potential. This technique, of course, may result in an electric current flowing through the upstream flow path under certain circumstances. Further, this technique would permit the environmental noise to be grounded near the aperture electrode, rather than at the package panel, thereby introducing other potential errors.

Another technique utilized in the prior art is a drip chamber, such as described in U.S. Pat. Nos. 3,979,669 granted Sept. 7, 1976 in the name of Godin, entitled "Particle Analyzing System", U.S. Pat. Nos. 3,340,470 and 3,340,471 both granted Sept. 5, 1967 in the name of J. R. Coulter, Jr. and entitled "Flow-Through Sample Apparatus For Use With Electrical Particle Study Device". In the aforementioned three patents, the flow path is broken by using a drip chamber, thereby causing an air gap within the flow path. This air gap acts as an open circuit and is designed to eliminate current flow in the flow path.

Another technique utilized in the prior art is a coiled tube, such as shown in U.S. Pat. No. 3,982,182 granted Sept. 21, 1976 in the name of Walter R. Hogg, entitled "Conductivity Cell For Particle Study Device" and U.S. Pat. No. 3,689,833 granted Sept. 5, 1972 in the name of Walter R. Hogg, entitled "Particle Analyzing Apparatus". The purpose of forming a coil in the tubes constituting the flow path is to greatly increase the over all length of the flow path within the limited space permitted in the cell counter. This increased length, in turn, increases the resistance of the flow path and thereby decreases the amount of current flowing through the flow path.

The latter two techniques utilized by the prior art to overcome the diversion of current to the flow path away from the aperture have two inherent disadvantages, that is, they require additional space within the package and they increase the cost. Further, neither technique is totally effective, particularly the coil technique which merely diverts less current. Even with the drip chamber, moisture or salt deposits along the side of the chamber can become electrically conductive and permit current to flow through the flow path and away from the aperture.

What is needed is a more effective, economical and compact solution to the problem of reducing the current through the flow path away from the aperture.

SUMMARY OF THE INVENTION

In accordance with one aspect of this invention, there is provided a blood cell analyzer of the type having a small aperture through which an electrically conductive fluid containing blood cells flows and a pair of electrodes are positioned on both sides of the aperture. The upstream electrode is at a reference voltage and the downstream electrode is at a different voltage. In addition, there is a sensor coupled between the electrodes to sense the resistance of the aperture. The analyzer further has suction means and a flow path containing the conductive fluid coupled from the downstream electrode to the suction means. The improvement is for electrically isolating the resistance of the aperture from the resistance of the fluid in the flow path and includes means for sensing the instantaneous voltage between the electrodes and means for coupling the sensed instantaneous voltage to the conductive fluid between the downstream electrode and the suction means.

DESCRIPTION OF THE DRAWINGS

By way of example, illustrative embodiments of the invention now will be described with reference to the accompanying drawings, in which.

DETAILED DESCRIPTION

Figure 1:
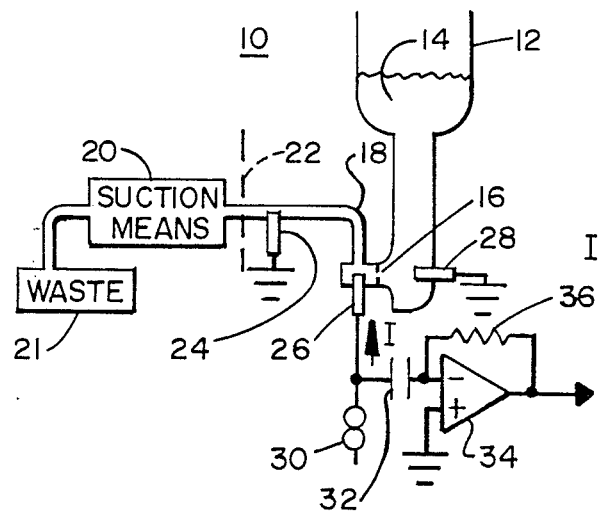
FIG. 1 is a schematic illustration of a blood cell counter, typical of the prior art.

Referring now to FIG. 1, a typical prior art blood cell counter 10 is shown and includes a sample supply chamber 12 having a fluid sample 14 contained therein. Sample 14 can be a diluted whole blood sample containing red and/or white blood cells. A Coulter type aperture 16 is placed in the sidewall towards the bottom of chamber 12, which historically has been termed an "aperture tube", and a flow path 18 connects the downstream side of aperture 16 to a suction means 20, the output of which is connected to a waste container 21. Suction means 20 is typically located outside of the counter 10 panels 22, indicated by the dashed line. Because the fluid within flow path 18 is electrically conductive, flow path 18 is grounded by an electrode 24 inserted therein and physically positioned at the point flow path 18 exits through panel 22. A grounded electrode 24 prevents any leakage signal from suction means 20 or environmental electric noise, such as sixty cycle hum or other signals in the environment, from being conducted through flow path 18 back to aperture 16.

The manner in which blood cells are counted as they pass through aperture 16 is well known in the art. Briefly, this is accomplished by placing electrodes 26 and 28 on either side of aperture 16 and providing a current I from a current source 30 from one to the other of electrodes 26 and 28. For example, the current I from a current source 30 can be applied to electrode 26 and electrode 28 can be placed at ground potential. Thus, the current I flows from electrode 26 through the sample 14 present in aperture 16 to electrode 28. Each time a blood cell flows through aperture 16, the resistance in aperture 16 is increased and the increased resistance is detected by voltage detector means attached between electrodes 26 and 28. The detector means includes a blocking capacitor 32 coupled between the positive electrode 26 and the negative input of an operational amplifier 34. The positive input of amplifier 34 is coupled to ground. In addition, a feedback resistor 36 is provided from the output to the negative input of amplifier 34. The output of amplifier 34 is the instantaneous voltage across aperture 16 and each time a blood cell passes through aperture 16, a voltage pulse occurs at the output of amplifier 34. The amplitude and number of pulses then can be detected, measured and counted to manifest the type of blood cell and cell count for the sample 14.

Figure 2:
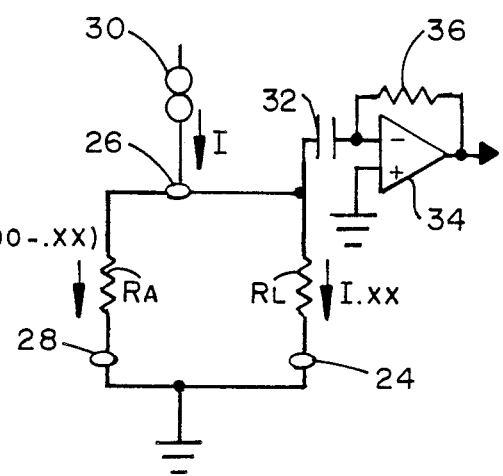
FIG. 2 is an electrical schematic diagram illustrating the problem with the prior art blood cell counter.

Referring now to FIG. 2, where like components are designated with like numerical identifications, a simple circuit diagram illustrates the problem with the configuration shown in FIG. 1. The resistance $R_A$ is the resistance of aperture 16 and the resistance $R_L$ is the resistance of flow path 18 from electrode 26 to electrode 24. As seen from FIG. 1, electrode 26 is at a positive potential relative to the two grounded electrodes 24 and 28. Thus, current I will be divided and flow through both aperture 16 (resistor $R_A$) and through flow path 18 (resistor $R_L$). The amount of the current division will depend upon the values of resistances $R_A$ and $R_L$ and these values, in turn, depend upon the distance separating the respective electrode pairs 26-28 and 24-26. Since the distance separating electrodes 24 and 26 is substantially greater than the distance separating electrodes 26 and 28, the value of $R_A$ is substantially greater than the value of resistance $R_L$.

In a compact blood cell analyzer, physical space will greatly limit the length of flow path 18, such that several percent of the current I from current source 30 can flow through flow path 18. This leakage current, $I_{xx}$, flowing through resistance $R_L$ will reduce the current, $I_{(1.00-xx)}$ flowing through resistance $R_A$, thereby reducing the definition of the pulse provided at the output of amplifier 34. This can result in pulses caused by platelet and small blood cell not being detected.

To avoid or minimize the above noted problem with respect to leakage current $I_{xx}$, prior art devices either drastically increased the length of flow path 18 by using a coiled pipe configuration in order to increase the value of resistance $R_L$, or provided a physical break in the electrical conductivity of the liquid by utilizing a drip chamber within flow path 18. As previously noted, neither of these techniques are one hundred percent effective and neither is available for use in a blood cell analyzer 10 designed to be compact. Thus, an alternate method must be utilized to reduce the leakage current $I_{xx}$ through resistance $R_L$ manifesting flow path 18.

Figure 3:
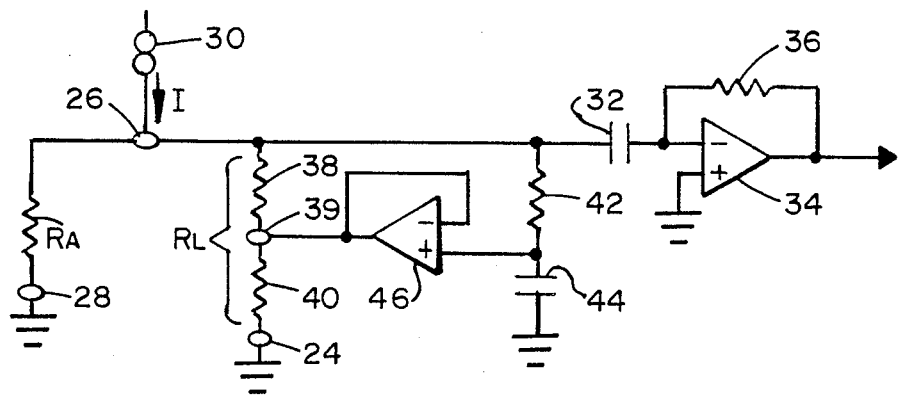
FIG. 3 is an electrical schematic diagram illustrating the solution to the problem illustrated in FIG. 2.

Referring now to FIG. 3, an electrical schematic diagram is shown which accomplishes the goal of eliminating the leakage current $I_{xx}$ flowing through resistance $R_L$. In FIG. 3, like components previously described are given like numeric designations. In FIG. 3, the flow path 18 line resistance $R_L$ is broken up into a lower line resistance 38 and an upper line resistance 40. In order to eliminate the leakage current $I_{xx}$ flowing through resistance $R_L$, the voltage level at a point 39 between lower line resistance 38 and upper line resistance 40 is forced to a value equal to the voltage applied between upper line resistance 40 and current source 30. In other words, the voltage at point 39 is made equal to the voltage at electrode 26. By making the voltage on both sides of lower line resistance 38 the same, no current whatsoever can flow through lower line resistance 38, and hence the leakage current $I_{xx}$ is reduced to zero.

The circuitry used to force point 39 to the same voltage as electrode 26, which varies upon the presence of a blood cell in aperture 16, includes a resistor 42 and a capacitor 44 coupled in series between electrode 26 and ground. The junction between resistor 42 and capacitor 44 is coupled to the positive input of a high impedance amplifier 46, the output of which is coupled to the negative input thereof and to point 39. Coupled in this manner, amplifier 46 acts as a voltage follower for providing the voltage applied to its input to its output. Since amplifier 46 has a very high input impedance and capacitor 44 acts as an open circuit to d.c. current, the voltage applied to the positive input of amplifier 46 is virtually identical to the voltage appearing at electrode 26. Thus, the voltage coupled to point 39 from the output of amplifier 46 is equal to the voltage at electrode 26. Since both sides of resistance 38 are now at the same voltage, no leakage current $I_{xx}$ can flow through lower line resistance 38 and, accordingly, all of the current I from current source 30 flows through the aperture resistance $R_A$.

Figure 4:
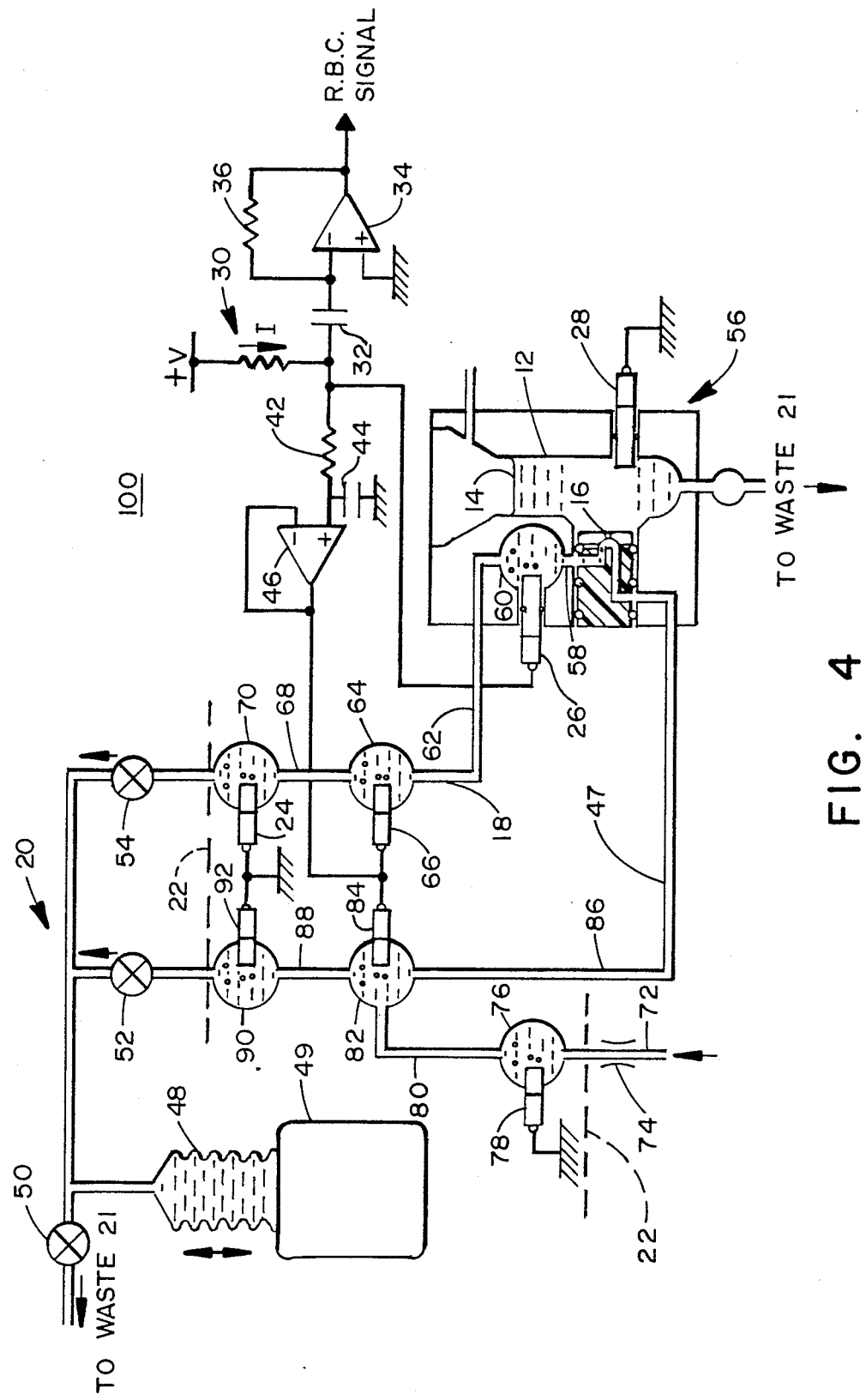
FIG. 4 is a schematic diagram illustrating the improved apparatus for a blood cell counter.

Referring now to FIG. 4, a specific implementation of a red blood cell counter 100, incorporating the inventive concept described with respect to FIG. 3, is shown.

Again, previously described components are given like numerical designations in FIG. 4. Cell counter 100 additionally includes a sweep flow path 47 utilized to sweep away the counted red blood cells. Such a path is described in more detail in U.S. Pat. No. 4,014,611, granted Mar. 29, 1977 in the name of Simpson et al and entitled, "Aperture Module For Use In Particle Testing Apparatus". It should be noted that the same leakage current problem, as previously described with respect to flow path 18, also exists with respect to sweep flow path 47 and the same solution described in FIG. 3 will be utilized to eliminate leakage current flow within the fluid contained in sweep flow path 47.

Suction means 20 includes a bellows device 48, an associated weight 49, an output valve 50 and a pair of input valves 52 and 54. Suction means 20 operates in the same manner as described in U.S. Pat. No. 4,631,483, granted Dec. 23, 1986 in the name of Proni et al and entitled, "Particle Analyzing Apparatus And Method Of Moving Particles Inceptions Through Such Apparatus". Briefly, bellows device 48 is expanded or contracted by moving weight 49 up or down, as viewed in FIG. 4, thereby creating a suction when weight 49 moves down and pressure when weight 49 moves up. During the suction phase, or downward movement of weight 49, one or both of valves 52 and 54 are opened and valve 50 is closed so as to permit fluid to flow from the fluid paths 18 and 47 into bellows 48. During the pressure phase, or upward movement of weight 49, both valves 52 and 54 are closed and output valve 50 is opened so as to permit the fluid which was drawn into bellows 48 during the suction phase to be expelled through valve 50 to the waste container 21.

The cell counting function is performed in a blood cell counter block or aperture module 56, which includes sample supply chamber 12 having aperture 16 in one sidewall thereof and grounded electrode 28 extending therein to contact the blood cell containing fluid sample 14. Grounded electrode 28 should be secured using O-rings or other similar sealing techniques to provide a fluid tight seal to prevent the leakage of sample 14 out of chamber 12. Since the fluid and cells of sample 14 flow from chamber 12 through aperture 16, the fluid 14 in chamber 12 is considered upstream from aperture 16. Similarly, grounded electrode 28 is considered to be the upstream electrode relative to aperture 16 and power electrode 26 is considered to be the downstream electrode.

On the downstream side of aperture 16, flow path 18 includes a flow path 58 connected between aperture 16 and to an electrode chamber 60 containing electrode 26. Electrode 26 is sealed in electrode chamber 60 by conventional fluid tight sealing means, such as an O-ring. A second flow path 62 connects the downstream side of electrode chamber 60 to another electrode chamber 64, into which is sealed an electrode 66. The downstream side of electrode chamber 64 is coupled through a flow path 68 to another electrode chamber 70, into which electrode 24 is sealed, and the downstream side of electrode chamber 70 is coupled to valve 54. Thus, when valve 54 is open and bellows device 48 provides suction, fluid travels away from aperture 16, through flow paths 58, 62 and 68 and valve 54 to the waste container 21. As previously mentioned, electrode 24 is coupled to ground and is physically positioned in chamber 70 adjacent to the outer package panel 22. With this positioning, electrode 24 grounds any current, due to environmental electrical noise, flowing through the flow paths from chamber 70 to suction means 20, so as to avoid electrical interference within the blood cell counter 100.

The sweep function is performed by providing an appropriate sweep fluid under pressure through a flow path 72 and a flow restrictor 74 into an electrode chamber 76, which contains a grounded electrode 78. Chamber 76 and electrode 78 are positioned physically close to panel 22 and serve the same purpose as electrode 24 in electrode chamber 70, that is, to ground the environmental electrical noise flowing in the fluid upstream of chamber 76. From chamber 76, the sweep fluid flows through a flow path 80 to an electrode chamber 82, which includes an electrode 84 sealed therein. There are two exits from chamber 82. The normally used exit is coupled to a flow path 86 to provide the sweep fluid under pressure into block 56 in a direction perpendicular to the direction of fluid flow through aperture 16. This fluid forces any blood cell flowing through aperture 16 away from aperture 16 to avoid it interfering in the electric field created through aperture 16, thereby eliminating a potential duplicate count.

The second exit from chamber 82 is through a flow path 88 to an electrode chamber 90, into which is sealed an electrode 92. Electrode 92 is grounded and serves the same function as electrodes 78 and 24, that is, to prevent environmental electrical noise interference from passing through the fluid contained in flow path 88. From electrode chamber 90, the fluid can be applied through valve 52, when open, to be drawn by bellows device 48 to waste container 21. Under normal circumstances, valve 52 is closed and the fluid applied under pressure through fluid path 72 is applied to sweep cells away from aperture 16. However, because of the presence of electrodes 78, 84 and 92, gas bubbles, as the result of hydrolysis, will occur within the sweep fluid and these are collected in the upper portion of chambers 82 and 90. Periodically it is necessary to purge the gas that builds up in electrode chambers 82 and 90 and, at this point in time, valve 52 is opened for a short time.

As seen in FIG. 4, electrodes 24, 78 and 92 are all grounded and positioned near panel 22. As previously mentioned, the grounding of electrodes 24, 78 and 92 isolates the circuitry within the cell counter 100 from electrical noise external to the cell counter 100. This grounding also creates an electrical path from electrode 26 to each of the grounded electrodes. In order to break up that electrical path, the output from high impedance amplifier 46 is coupled to electrodes 66 and 84. As previously discussed with respect to FIG. 3, the voltage at the output of amplifier 46 is the same as the voltage applied to electrode 26 from current source 30. These electrodes 66 and 84 are the equivalent of point 39 in FIG. 3. Thus, a zero voltage difference exists between electrode 26 and both electrode 66 and electrode 84 through their respective flow path 62 and 86. With such a zero voltage difference, no current can flow through either flow path 62 or 86. Thus, all of the current I provided from current source 30 to electrode 26 flows through aperture 16 to electrode 28.

FIG. 4 has been described as including a sweep flow path generally shown by flow paths 72, 80 and 86. As is well known, such a flow path is normally utilized only with respect to a blood cell counter 100 used to count red blood cells and not a blood cell counter used to count white blood cells. In a white blood cell counter, elements 52, 90, 92, 88, 82, 84, 80, 72, 74, 76, 78 and 86 would be eliminated from the components shown in FIG. 4.

What is claimed is:

1. In a particle analyzer of the type having a small aperture through which an electrically conductive fluid containing particles flows and a pair of electrodes positioned on both sides of said aperture, the upstream electrode being at a reference voltage and the downstream electrode being at a different voltage, a sensor being coupled between said electrodes to sense the resistance of said aperture, said analyzer further having suction means and a flow path containing said conductive fluid coupled from said downstream electrode to said suction means, the improvement for electrically isolating said resistance of said aperture from the resistance of said fluid in said flow path comprising:

sensing means for sensing the instantaneous voltage between said electrodes; and coupling means for coupling said sensed instantaneous voltage to said conductive fluid between said downstream electrode and said suction means.

2. The invention according to claim 1 wherein said coupling means includes a second pair of electrodes within said flow path, one of said second pair of electrodes being coupled to reference voltage and the other of said second pair of electrodes being coupled to said sensed instantaneous voltage.

3. The invention according to claim 2 wherein said other of said second pair of electrodes is positioned between said one of said second pair of electrodes and said downstream electrode.

4. The invention according to claim 1 wherein said analyzer further includes a sweep flow path coupled adjacent to said aperture, said sweep flow path containing a conductive fluid and said coupling means further couples said sensed instantaneous voltage to said sweep flow path conductive fluid at a position remote from said downstream electrode.

5. The invention according to claim 4 wherein said coupling means includes a second pair of electrodes within said sweep flow path, one of said second pair of electrodes being coupled to reference voltage and the other of said second pair of electrodes being coupled to said sensed instantaneous voltage.

6. The invention according to claim 5 wherein said other of said second pair of electrodes is positioned between said one of said second pair of electrodes and said downstream electrode.

7. The invention according to claim 4 wherein said coupling means includes a second and third pair of electrodes within each of said first mentioned flow path and said sweep flow path, respectively one of said electrodes of each of said second or third pair of electrodes being coupled to reference voltage and the other electrode of each of said second or third pair of electrodes being coupled to said sensed instantaneous voltage.

8. The invention according to claim 7 wherein said other electrode of each of said second and third pair of electrodes is positioned between said one electrode of each of said second and third pairs of electrodes and said downstream electrode respectively.

9. A particle analyzer comprising:

holding means for holding a conductive fluid containing particles to be analyzed, said holding means including an aperture through which said fluid and particles pass;

first and second measuring electrodes positioned on each side of said aperture;

electrical means for providing a constant current from one to the other of said measuring electrodes and for measuring the voltage between said measuring electrodes;

fluid handling means for causing the fluid to flow through said aperture, said fluid handling means including a flow path from one side of said aperture; and nulling means for providing a null voltage in said flow path to eliminate current flow through the fluid in said flow path;

said measuring electrode positioned on the side of said aperture opposite to said flow path being at a reference voltage and said null voltage being equal to said measured voltage.

10. The invention according to claim 9 wherein said flow path includes one of said measuring electrodes and a third electrode positioned therein remote from said one measuring electrode, said null voltage being provided to said third electrode.

11. The invention according to claim 10 wherein said fluid handling means includes a second flow path having a fourth electrode positioned therein, said second flow path being downstream from said third electrode, said fourth electrode being at said reference voltage.

12. The invention according to claim 11 wherein said analyzer includes a panel means through which said second flow path exits and said fourth electrode is positioned juxtaposed to said panel means and isolates said analyzer against environmental noise voltages flowing through said fluid in said fluid handling means from within said panel means.

13. The invention according to claim 12 wherein said null voltage is said measured voltage provided through a high input impedance amplifier isolated from said aperture.

14. The invention according to claim 9 wherein said analyzer further includes a sweep flow path for directing a conductive fluid against the downstream side of said aperture and said nulling means further provides said null voltage to said sweep flow path.

15. The invention according to claim 14 wherein said fluid handling means has one of said measuring electrodes positioned therein and is in fluid communication with said sweep flow path and said sweep flow path includes a third electrode positioned therein remote from said one measuring electrode, said null voltage being provided to said third electrode.

16. The invention according to claim 15 wherein said sweep flow path includes a fourth electrode positioned therein remote from said third electrode, so that said third electrode is between said aperture and said fourth electrode, said fourth electrode being at said reference voltage.

17. The invention according to claim 16 wherein said analyzer includes panel means through which said sweep flow path exits and said fourth electrode is positioned juxtaposed to said panel means and isolates said analyzer from environmental noise voltages flowing through said fluid in said sweep flowpath away from said panel means.

18. The invention according to claim 17 wherein said first mentioned flow path includes said one measuring electrode and further includes a fifth electrode positioned therein remote from said one measuring electrode, said null voltage being provided to said fifth electrode.

19. The invention according to claim 18 wherein said fluid handling means includes a second flow path having a sixth electrode positioned therein, said second flow path being downstream from said fifth electrode, said sixth electrode being at said reference voltage.

20. The invention according to claim 19 wherein said second flow path exits through said panel means and said sixth electrode is positioned juxtaposed to said panel means and isolates said analyzer from environmental noise voltages flowing through said fluid handling means from within said panel means.

21. The invention according to claim 20 wherein said null voltage is said measured voltage provided through a high input impedance amplifier isolated from said aperture.

22. The invention according to claim 9 wherein said null voltage is said measured voltage provided through a high input impedance amplifier isolated from said aperture.

* * * * *